United States Patent [19]

Nichols

[11] Patent Number: 5,188,602
[45] Date of Patent: Feb. 23, 1993

[54] METHOD AND DEVICE FOR DELIVERING HEAT TO HOLLOW BODY ORGANS

[75] Inventor: Colin J. Nichols, Fremont, Calif.

[73] Assignee: Interventional Thermodynamics, Inc., Mountain View, Calif.

[21] Appl. No.: 895,579

[22] Filed: Jun. 8, 1992

Related U.S. Application Data

[63] Continuation of Ser. No. 551,971, Jul. 12, 1990, abandoned.

[51] Int. Cl.$^5$ .............................................. A61F 7/12
[52] U.S. Cl. ................................. 604/113; 604/49; 604/96; 604/107; 128/401
[58] Field of Search .......................... 604/113–114, 604/96, 105–107, 49; 606/33, 49; 128/784–786, 804, 401

[56] References Cited

U.S. PATENT DOCUMENTS

| | | | |
|---|---|---|---|
| 3,901,224 | 8/1975 | Bucalo . | |
| 4,030,505 | 6/1977 | Tessler | 604/105 X |
| 4,160,455 | 7/1979 | Law . | |
| 4,375,220 | 3/1983 | Matvias . | |
| 4,469,103 | 9/1984 | Barrett . | |
| 4,638,436 | 1/1987 | Badger et al. . | |
| 4,676,258 | 6/1987 | Inokuchi et al. . | |
| 4,754,752 | 7/1988 | Ginsburg et al. | 604/113 X |
| 4,869,248 | 9/1989 | Narula . | |
| 4,946,440 | 8/1990 | Hall | 604/95 |
| 4,979,948 | 12/1990 | Geddes et al. | 606/33 |

FOREIGN PATENT DOCUMENTS

| | | |
|---|---|---|
| 3725691 | 3/1988 | Fed. Rep. of Germany . |
| 281489 | 9/1970 | U.S.S.R. . |
| 1329781 | 8/1987 | U.S.S.R. . |

OTHER PUBLICATIONS

Becker et al. (1989) Radiology 171:235–240.
Becker et al. (1989) Work in Progress Paper #1354, RSNA Meeting, Nov. 1989.
Coleman, (1988) SCVIR pp. 214–219.
Salomonowitz et al. (1984) Arch. Surg. 119:725–729.
Getrajdman et al. (1985) Invest. Radiol. 20:393–398.
Getrajdman et al. (1986) Invest. Radiol. 21:400–403.
Remley et al. (1986) Invest. Radiol. 21:396–399.
Becker et al. (1988) Radiology 167:63–68.

*Primary Examiner*—C. Fred Rosenbaum
*Assistant Examiner*—C. Maglione
*Attorney, Agent, or Firm*—Townsend and Townsend

[57] ABSTRACT

A catheter for thermally treating a hollow body organ includes a first flexible elongate member having a heater element at or near its distal end. A second flexible elongate member may be slidably disposed within a central lumen of the first flexible elongate member and may include an occluding means, such as an inflatable balloon, at its distal end. By first inserting the distal end of the second flexible elongate member within a hollow body organ or connecting region, the heater element on the first flexible elongate member may then be positioned and repositioned by axially translating the first flexible elongate member over the exterior of the second flexible elongate member. A collapsible shield may also be provided about the exposed heater element on the first flexible elongate member. The shield typically comprises a cylinder having a plurality of axial slots near its distal end. A plurality of ribs defined by the slots may be expanded radially outward by compressing the cylinder in the distal direction or by releasing tension which has maintained the shield in a radially collapsed configuration. Once expanded, the shield may be rotated to effect mixing of the fluid surrounding the catheter.

45 Claims, 5 Drawing Sheets

METHOD AND DEVICE FOR DELIVERING HEAT TO HOLLOW BODY ORGANS

This is a continuation of Ser. No. 07/551,971, filed Jul. 12, 1990, now abandoned.

BACKGROUND OF THE INVENTION

1. Field of the Invention

The present invention relates generally to methods and apparatus for delivering heat to hollow body organs. More particularly, the present invention relates to methods and devices for positioning a heat source within the interior of a hollow body organ.

In recent years, a variety of "least-invasive" surgical procedures has been developed as alternatives to conventional "open" surgery. While least-invasive surgical procedures have no fixed definition, they are generally characterized by use of specialized surgical tools in combination with visual or radiographic imaging techniques. The specialized tool is generally inserted through an open body orifice or a small surgical incision, and the tool is then positioned within the body using the imaging technique to allow manipulation of the organ or structure to be treated. A common example of least-invasive surgery is arthroscopic knee surgery, where penetration of the surgical tools is minimal. Less-accessible body organs, such as heart and interior blood vessels, may be reached by specialized catheters which may be routed through the vascular system over relatively long distances. Exemplary of such vascular catheters are balloon dilatation catheters which are used to expand regions of stenosis within diseased blood vessels.

Of particular interest to the present invention are least-invasive surgical techniques which rely on a catheter to deliver heat to the interior of a hollow body organ. As described in detail in co-pending application Ser. No. 07/407,839 and the delivery of heat may be used for deactivating or ablating a diseased body organ, such as a gallbladder, appendix, uterus, kidney, or the like, as well as for blocking other body lumens, such as blood vessels. Such catheters might also find use for other purposes, such as for thermal treatment of tumors, and the like.

The use of catheters to deliver heat internally within hollow body organs is problematic in certain respects. First, it can be difficult to properly position catheters at a desired location within a hollow body organ or adjacent connecting region. Such positioning difficulties can be exacerbated when the catheter includes a distal balloon for sealing such a connecting region in order to inhibit the loss of a thermally conductive medium which may be introduced to the body organ. For example, once the catheter tip is in place with the distal balloon inflated, it is difficult to reposition the catheter in order to relocate a heating element located on the catheter.

A second difficulty arises when using heating elements on the catheter, such as resistance coils, which are externally disposed in order to enhance heating efficiency. In that case, the catheter must be carefully positioned to avoid direct contact between the heating element and the inner wall of the hollow body organ. Direct contact can cause excessive heating, tissue adherence, and potential damage to adjacent body organs. The proper positioning of the catheter heating element relative to an entrapped fluid within the organ is difficult when the catheter is first placed within the hollow body organ and becomes more difficult as the catheter (and optionally a sealing balloon) is repositioned one or more times during a single treatment procedure.

For these reasons, it would be desirable to provide improved apparatus and methods for delivering heat to the interior of hollow body organs. It would be particularly desirable if catheters were adapted to facilitate positioning and repositioning of a heating element external to the catheter within the hollow body organ and were further adapted to provide for sealing of adjacent regions which connect to the hollow body organ. In particular, it would be desirable if the catheter heating element could be repositioned while an inflatable balloon remains in place to effect sealing of a region connecting with the hollow body organ. Desirably, the catheter will further include a shield arranged about the external heating element to prevent direct contact between the heating element and the interior wall of the hollow body organ. Desirably, such a shield may be movable in order to mix a fluid content of the hollow body organ to enhance temperature uniformity therein. Preferably, the catheter will be easy to manufacture, will provide access for introducing a thermally conductive medium into the interior of the hollow body organ, and will be suitable for distributing heat in a predetermined pattern within the hollow body organ and connecting region(s).

2. Description of the Background Art

Coleman, *Non-Surgical Ablation of the Gallbladder,* Proc. 1988 SCVIR, pp 214–219, is a review article discussing various techniques for non-surgical gallbladder ablation, including the work of Salomonowitz and of Getrajdman relating to the introduction of an externally heated medium to induce fibrosis of the gallbladder. The article further presents data demonstrating thermal ablation of a dog's gallbladder after open surgical injection of hot contrast media. The work of Salomonowitz is described in Salomonowitz et al. (1984) Arch. Surg. 119:725–729. The work of Getrajdman is described in Getrajdman et al. (1985) Invest. Radiol. 20:393–398 and Getrajdman et al. (1986) Invest. Radiol. 21:400–403. The use of sclerosing agents to induce gallbladder fibrosis is described in Remley et al. (1986) Invest. Radiol. 21:396–399. See also Becker et al. (1988) Radiology 167:63–68; Becker et al. (1989) Radiology 171:235–240; and Becker et al. (1989) Work in Progress Paper #1354, RSNA Meeting, November 1989. U.S. Pat. No. 4,160,455, describes a device for internally heating a body cavity for therapy, where the heat is intended to inhibit the growth of tumor cells. German Patent 37 25 691 describes a catheter combining a heater at its distal tip and a balloon proximate the heater, where the heater is not directly exposed to the fluid environment surrounding the catheter tip. U.S. Pat. No. 4,869,248, describes a thermal ablation catheter having a resistive heating loop at its distal end. Other patent documents describing heated or cooled catheters include U.S. Pat. Nos. 4,676,258; 4,638,436; 4,469,103; 4,375,220; 3,901,224; USSR 1329-781-A; and USSR 281489.

SUMMARY OF THE INVENTION

The present invention comprises a catheter apparatus and method for heating the interior of a hollow body organ, such as a gallbladder, uterus, appendix, kidney, blood vessel, and the like. The apparatus comprises a first flexible elongate member having a proximal end, a distal end, and means for heating an environment surrounding the catheter near said distal end.

In a first embodiment, the catheter apparatus further includes a second smaller diameter flexible elongate member slidably disposed within a central lumen extending through the first flexible elongate member, where the second flexible elongate member usually includes means for positioning its distal end within the hollow body organ or a region connecting therewith. The means for positioning may include an axial guidewire lumen or a fixed guidewire attached to the distal end of the second flexible elongate member. The second flexible elongate member may further include a device for sealing or occluding a connecting region, such as an inflatable balloon disposed at the distal end of the member. In use, the catheter can be initially positioned in a desired location, optionally with the balloon inflated in place to occlude the connecting region and inhibit loss of a thermally conductive medium from the interior of the organ. The heater can be repositioned over the second flexible elongate member simply by sliding the first flexible elongate member in a forward and/or rearward direction. In this way, heat can be applied anywhere along a path defined by the second flexible elongate member while allowing the balloon to remain in position blocking the connecting region.

In a second embodiment, means are formed on the first flexible elongate member for expanding a shield about the heating means. In the preferred embodiment, the means for expanding a shield comprises a cylinder mounted over the exterior of the first flexible elongate member, where the cylinder includes a plurality of axial slits or apertures disposed near its distal end. The distal end of the cylinder is generally fixed to the distal end of the first flexible member so that pushing on the cylinder compresses the distal end, causing individual elements or ribs formed by the slits to move outward to form a protective cage about the heater element. As the ribs move outward, large spaces between adjacent ribs are formed, which spaces allow the free circulation of fluid being heated while maintaining a protective cage around the heating element to prevent unintended contact with the interior wall of the organ.

In a third embodiment, the shield means on the first flexible elongate member is rotatable about the axis of the catheter. Rotation of the shield can facilitate mixing of the thermally conductive medium thus enhancing temperature uniformity within the hollow body organ.

The catheter and method of the present invention thus facilitate positioning and repositioning of a heating element within the hollow body organ and connecting region(s) while enhancing temperature uniformity. The catheter can further minimize the likelihood that the heating element will directly contact the interior of said organ, provide for sealing of a connecting region, and allow the introduction of a thermally conductive medium through one or more lumens formed in the catheter. The catheters of the present invention are easy to manufacture and suitable for use in any therapeutic method which relies on the application of heat to a hollow body organ or duct.

DESCRIPTION OF THE SPECIFIC EMBODIMENTS

According to the present invention, apparatus and methods are provided for heating the interior of a wide variety of hollow body organs and passages, particularly including those which have an endothelial lining, mucous membrane, or other internal surface which may be thermally injured to inactivate the organ and usually to induce necrosis and subsequent fibrosis of the organ itself. Alternatively, the present invention may be used to provide thermal therapy where the temperature of the surrounding tissue is raised, particularly in the treatment of solid tumors and other neoplastic diseases. Exemplary hollow body organs include the gallbladder, the appendix, the uterus, the kidney, and the like. Exemplary hollow body passages include blood vessels, fistulas, and the like. When the intent is to inactivate, the hollow body organ will usually be diseased or in some way abnormal prior to treatment according to the present invention. When the desire is to thermally treat surrounding tissue, an organ or passage may serve merely as an access route. In other cases, it may be desirable to ablate and destroy apparently healthy body organs or parts in order to achieve a desired purpose, e.g., blockage of a blood vessel in a varicocele procedure. For convenience hereinafter, the phrase "hollow body organ" is intended to embrace both hollow body organs and hollow body passages.

The apparatus of the present invention comprises a catheter including a first flexible elongate member having a proximate and distal end. The length of the first flexible elongate member will vary depending on the intended use of the catheter, typically being in the range from about 10 to 100 cm, usually being in the range from about 10 to 50 cm, and more usually being in the range from about 10 to 20 cm, although longer structures may be provided for certain intravascular applications. Usually, the first flexible elongate member will have a tubular geometry and include at least one axial lumen extending from the proximal end to the distal end, although in certain embodiments it may be possible to employ a substantially rigid structure. The first flexible elongate member will typically be formed as an extruded organic polymer, such as silicone rubber, polyurethane, polyvinylchloride, nylon, and the like. The first elongate member should have sufficient column strength to avoid buckling when it is axially compressed during usage.

An external heating means will be located at or near the distal end of the first flexible elongate member, typically being located within about 10 cm of the distal tip, more typically being located within about 5 cm of the distal tip, and usually being located within 1 cm or less of the distal tip. The heating means will generally provide a heated surface for convectively heating fluid surrounding the catheter tip, typically comprising a resistive heating surface, such as a wire coil wrapped around the exterior surface of the first flexible elongate member. While resistance heating elements will generally be the most convenient, it may be possible to provide other energy sources, such as radio frequency, laser energy, or the like for raising the temperature of the heated surface and/or the surrounding fluid. In all cases, the heated surface of the heating means will be disposed externally on or near the surface of the first flexible elongate member in order to enhance heat transfer to the surrounding environment, as described in more detail hereinafter.

The heating means may comprise a single-point heating source, for example, a single-cartridge heater, extending over a limited distance, usually 3 mm or less. Often, however, it is desirable to provide a distributed heating source over an extended axial length greater than 3 mm, usually being in the range from about 3 mm to 6 cm, more usually being in the range from about 1 cm to 4 cm, and most usually being in the range from about 1.5 cm to 3 cm. Such elongate heating surfaces will preferably be flexible over their entire length when mounted on the first flexible elongate member. In this way, the desired flexibility of the catheter will not be substantially diminished near the distal tip; more frequently, a higher degree of flexibility is required in order to allow entry into constricted, relatively tortuous ducts and passages connecting with a hollow body organ.

Flexible elongate heating sources will typically comprise either a plurality of spaced-apart discrete heating elements, e.g., a plurality of single-point heating sources, such as cartridge heaters, or a continuously wound heating source, such as a heating coil wrapped around the exterior of the first flexible elongate member. In either case, it may be desirable to adapt the axially elongated heating source to deliver a variable heat flux over its length. In particular, the heat flux may be reduced in regions where the heating source will be within a restricted volume of a thermally conductive medium and relatively increased where the heating source will be in a larger volume of a thermally conductive medium. In this way, a relatively uniform temperature profile within the hollow body organ and optionally within connecting ducts and regions may be achieved.

A system will usually be provided for controlling the temperature to which the environment surrounding the catheter is heated by the heat means. Such a temperature-control system may comprise a feedback controller where a temperature-sensing element (typically a thermocouple or thermistor) is mounted on the catheter at a location chosen to accurately measure the heated environment. The energy delivered to the heating means may then be regulated based on the measured temperature of the surrounding environment. Alternatively, numerous auto-regulating heaters are available which do not require a separate control loop.

In a first embodiment of the present invention, a second flexible elongate member is slidably disposed within an axial lumen of the first flexible elongate member. The second flexible elongate member includes an occlusion means at or near its distal end so that the second flexible elongate member may be positioned and the occlusion means actuated to occlude a region or duct connecting with the hollow body organ. The occluding means is conveniently an inflatable balloon and usually, but not necessarily, inflation of the balloon will lodge the distal end of the second elongate member within the connecting region. The heating means of the first flexible elongate member may then be positioned and repositioned within the hollow body organ and connecting regions simply by translating the first flexible elongate member back and forth along the second flexible elongate member, which possesses sufficient column strength to act as a rail or guide for the heating element. In this way, the heating element may be accurately positioned within the hollow body organ and connecting regions.

The second flexible elongate member will have a distal end and a proximal end and will typically have a length which is somewhat greater than that of the first flexible elongate member. The greater length allows the second flexible elongate member to extend beyond both the proximal and distal ends of the first flexible elongate member, thus allowing the first flexible elongate member to be translated over the second flexible elongate member while the treating physician may still manipulate the proximal end of the second flexible elongate member, which remains outside of the first member.

In its simplest form, the second flexible elongate member may simply be a guidewire. More usually, the second flexible elongate member will have a tubular geometry, including a central axial lumen for receiving a guidewire and one or more additional lumens for balloon inflation (as described hereinafter). The central lumen will be available for perfusion of a thermally conductive medium, aspiration, and the like, but it would be possible to form separate lumens for these purposes if desired. The second flexible elongate member will usually be formed as an extruded organic polymer, typically being silicone rubber, polyurethane, nylon, and the like.

The occlusion means will usually comprise an inflatable balloon located at or near the distal tip of the second flexible elongate member. Occlusion of the duct or passage is advantageous to prevent the outflow of heated solutions from the organ being treated. The balloon will typically be inflatable through an inflation lumen extending the length of the second flexible member from the proximal end to the location of the balloon. When inflated, the balloon will usually become anchored axially, allowing the first member to move over the second member to reposition the heater relative to the balloon. The balloon may be inflated with a thermally conductive medium when it is desired to provide for heat transfer through the balloon to the surface in contact with the balloon. Alternatively, the balloon may be inflated with a thermally insulating medium, such as carbon dioxide, when it is desired to limit heat transfer to the region in contact with the balloon.

In a second embodiment of the present invention, a means is provided on the first flexible elongate member for expanding a shield about the heating element while the heating element is positioned within the hollow body organ or connecting region. The shield means typically comprises an expandable cage which may be maintained in a collapsed configuration while the catheter is introduced to the hollow body organ and thereafter expanded to form a protective structure which prevents direct contact between the heating element and the inner wall of the hollow body organ. The expanded structure will be formed generally as a cage possessing a plurality of relatively large apertures or openings which permit free circulation of a thermally conductive medium within the hollow body organ so that the environment surrounding the catheter can be rapidly and uniformly heated.

Preferably, the shield means comprises a cylinder disposed coaxially about the first flexible elongate member. A region of the cylinder circumscribing the heating element is provided with a plurality of axial slits which define a like number of axial ribs which may be expanded outwardly by axial compression of the cylinder. Conveniently, the cylinder will extend the entire length of the first flexible elongate member, with the distal tip of the cylinder secured to the distal tip of the elongate member. In this way, the cylinder can be compressed simply by pushing on its proximal end, which will transmit the compression force to the shield region which is to be expanded.

Figure 1:
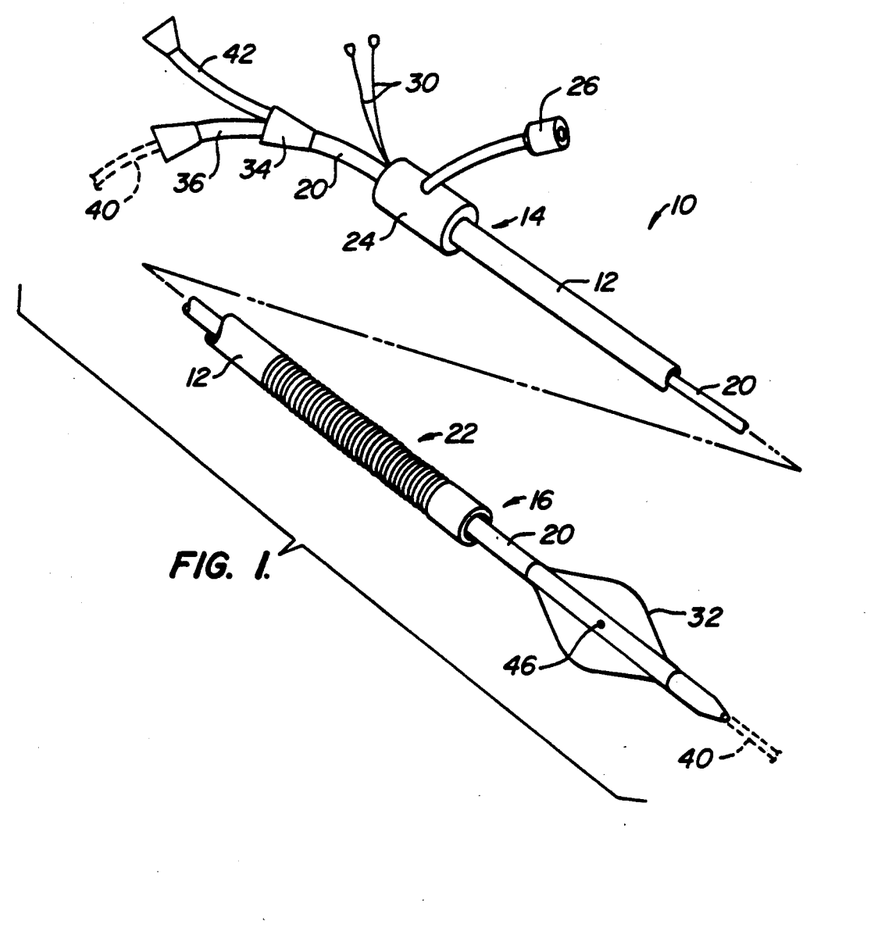
FIG. 1 is a perspective view of a first embodiment of the heating catheter of the present invention.
Figure 2:
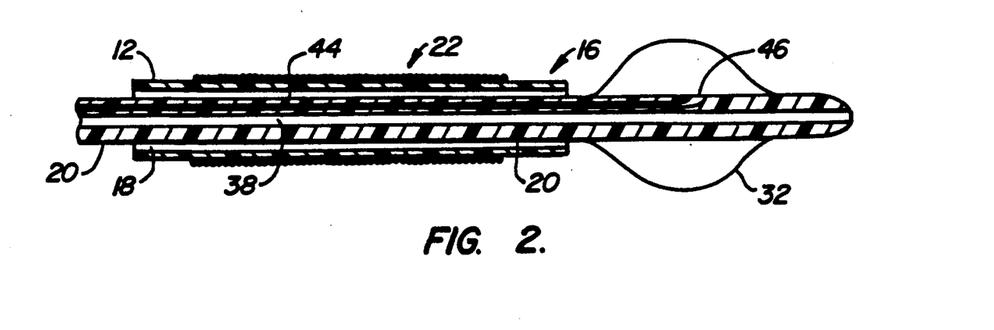
FIG. 2 is a detailed elevational view of the distal end of the catheter of FIG. 1, shown in cross-section.

Referring now to FIGS. 1 and 2, the construction of a first catheter 10 constructed in accordance with the principles of the present invention will be described. The catheter 10 includes a first flexible elongate member 12 having a proximal end 14 and a distal end 16. A central axial lumen 18 extends from the proximal end 14 to the distal end 16, and a second flexible elongate member 20 is slidably disposed therein.

The first flexible elongate member 12 includes a heating element 22 formed near its distal end 16 and a housing 24 secured to its proximal end 14. The housing 24 includes a connector 26 which provides for fluid access to the central lumen 18 and further provides a slidable seal about the second flexible elongate member 20. In this way, fluid may be introduced to the central lumen 18 and flowed in a distal direction with minimal loss from the proximal end of housing 24.

The heating element 22 preferably comprises a wire coil wrapped around the exterior of the first flexible elongate member 12. The number of windings, spacing of the windings, current capacity of the wire, and the like, will be selected based on the desired amount and profile of heat to be delivered. Current may be provided to the coil through a pair of connector wires 30 which extend outward from housing 24. The wires 30 will typically be extruded in place within the wall of first member 12 to allow convenient connection to the coil 22, but other connections will also be possible.

The second flexible elongate member 20 includes an inflatable balloon 32 located near its distal end and a branch ("Y") coupling 34 secured to its proximal end. The inflatable balloon 32 may be constructed in a conventional manner, and may comprise either a slack bladder which is inflatable to a predetermined diameter and geometry or, alternately, may comprise an expandable bladder which can be inflated to an increasing diameter or size as the internal pressure is increased. The construction of such balloons is well known in the art and amply described in the medical and patent literature. The dimensions of the balloon 32 will be selected to provide for occlusion within a desired portion of the hollow body organ and/or region connecting with the hollow body organ.

A first connector 36 is attached to the branch coupling 34 and provides for access to a central lumen 38 extending through the second elongate flexible member 20. Typically, a guidewire 40 may be introduced through the connector 36 and the central lumen 38 to provide for positioning of the catheter 10 in a conventional manner. The coupling 36 may also be used for introducing media, aspirating media, and the like. A second coupling member 42 is attached to the branch coupling 34 and connects to a balloon inflation lumen 44, which terminates at a port 46 within balloon member 32. In this way, the balloon member 32 may be inflated after the catheter has been positioned within the hollow body organ. A stopcock (not shown) may be utilized to maintain balloon inflation by closing the proximal end of connector 36.

Figure 3:
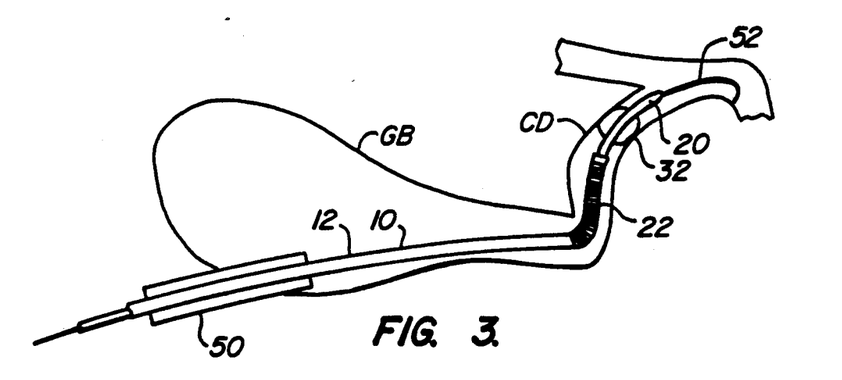
FIGS. 3 and 4 illustrate the method of the present invention using the catheter of FIG. 1 to heat a gallbladder.
Figure 4:
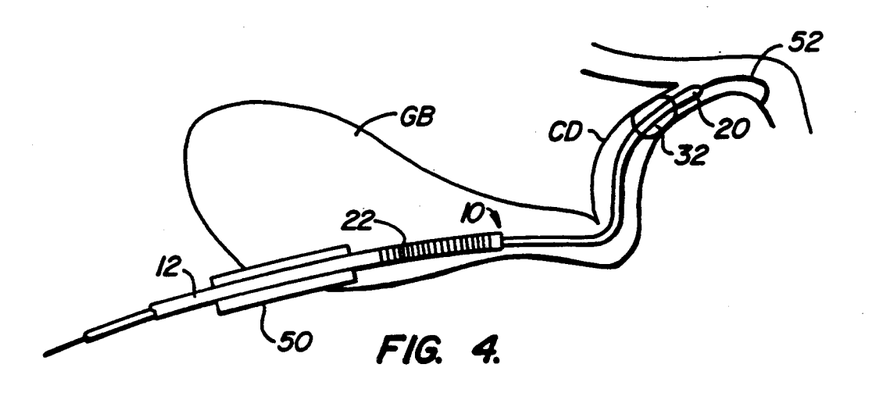

Referring now to FIGS. 3 and 4, use of the catheter 10 in ablating a gallbladder GB will be described. Gallbladder ablation will be desirable in cases of cholecystolithiasis, where the diseased gallbladder is likely to continue production of gallstones. Gallbladder ablation according to the present invention may be performed as generally described in co-pending application Ser. Nos. 07/407,839 and 07/529,077, the disclosures of which are incorporated herein by reference.

The catheter 10 may be introduced to the gallbladder GB via a trans-hepatic or sub-hepatic route using an insertion sheath 50. Using a guidewire 52, the distal tip of the second flexible elongate member 20 may be inserted into the cystic duct CD and the balloon 32 inflated as illustrated in FIG. 3. Inflation of the balloon 32 both anchors the distal end of the second flexible elongate member 20 within the cystic duct CD and occludes the bile duct so that a thermally conductive medium which is introduced to the gallbladder GB will not immediately drain through the duct.

The thermally conductive medium may be introduced through connector 26 (FIG. 2) so that it enters within the annular region remaining between the second flexible elongate member 20 and the interior wall of lumen 18 within the first flexible elongate member 12. After introducing the thermally conductive medium, the heater element 22 may be positioned by axially translating the first flexible elongate member 12 over the second flexible elongate member 20. As illustrated in FIG. 3, the heater element 22 lies substantially within the interior of the cystic duct CD, where a preselected amount of heat can be delivered to effect the desired ablation of that region. After treating the cystic duct CD, the heater element 22 can be moved in the proximal direction so that it lies substantially within the interior of the gallbladder GB (FIG. 4). In that position, a preselected amount of heat can be delivered in order to effect ablation of the much larger interior area of the gallbladder. The precise order in which the regions are ablated is not critical, and it will also be possible to introduce a thermally conductive medium at different times during the treatment procedure. In all cases, however, the present invention facilitates positioning of the heater element.

Referring now to FIGS. 5-8, a second embodiment of a heating catheter 60 constructed in accordance with the principles of the present invention will be described. The catheter 60 includes a first flexible elongate member 62 which is similar in most respects to the first flexible elongate member 12 illustrated in FIGS. 1 and 2. The first flexible elongate member 62 includes a housing 64 at its proximal end 66 and a branch connector 68 which allows access to a central lumen 70 extending through the first flexible elongate member 62. A heater 72 is disposed externally near the distal end of the first flexible elongate member 62, and a pair of connecting wires 74 extends outward through the proximal housing 64. Thus far, the description of the catheter 60 is generally similar to that of catheter 10 described hereinabove.

Figures 5, 6:
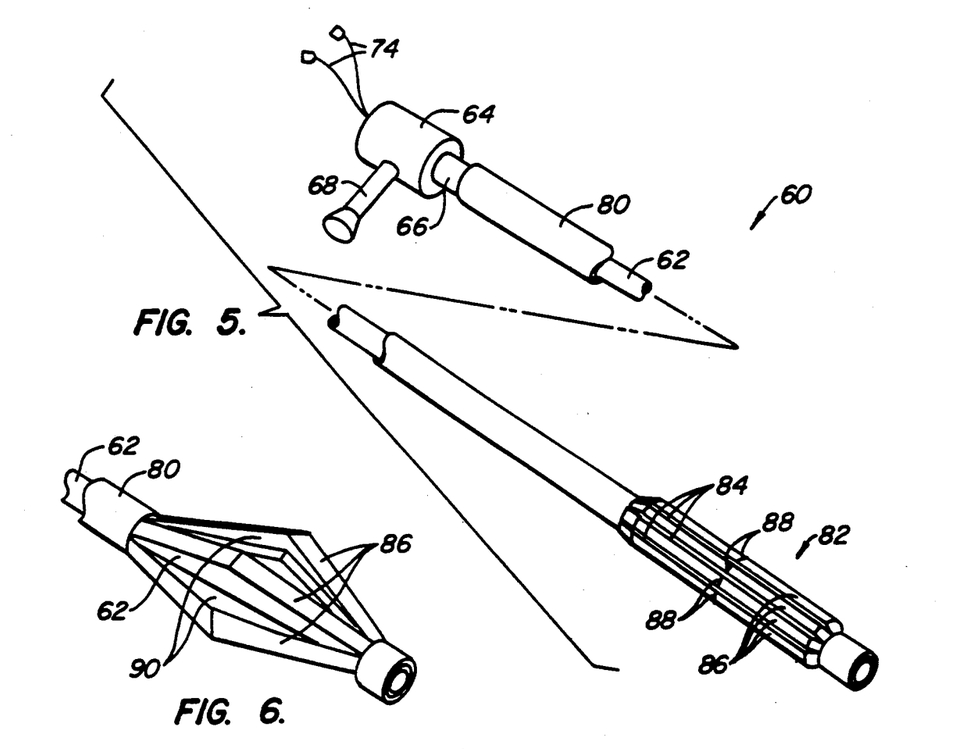
FIG. 5 is a perspective view of a second embodiment of the heating catheter of the present invention, shown with a protective shield in a collapsed configuration.
FIG. 6 is a perspective view of the distal end of the catheter of FIG. 5, shown with the protective shield in an expanded configuration.
Figure 7:
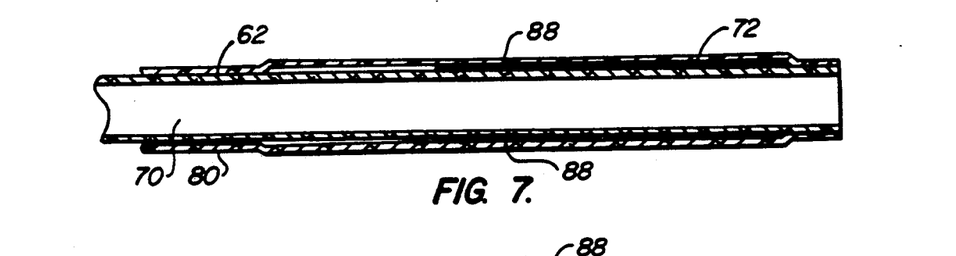
FIG. 7 is a detailed elevational view of the distal end of the catheter of FIG. 5, shown in cross-section.
Figure 8:
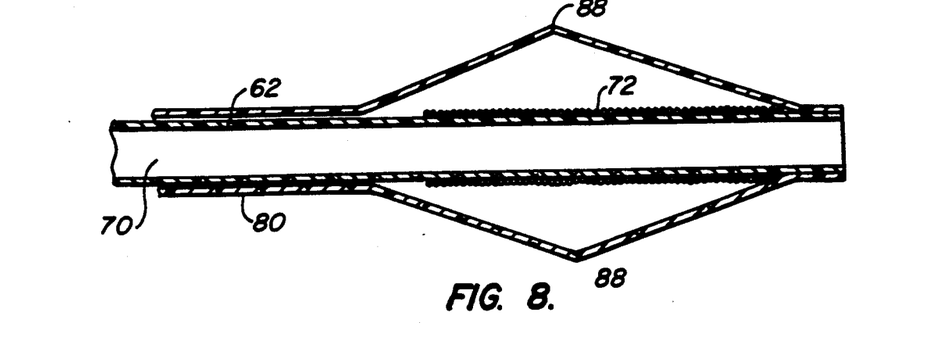
FIG. 8 is a detailed elevational view of the distal end of the catheter of FIG. 5, shown in cross-section with the protective shield in its expanded configuration.

A cylinder 80 is disposed coaxially about the exterior of the first flexible member 62. A shield region 82 is formed near the distal end of the cylinder 80, including a plurality of axial slits or apertures 84. The slits 84, in turn, define a plurality of axial members or ribs 86, which optionally include indentations 88 near their middle. The distal end of the cylinder 80 is secured to the distal end of the first flexible elongate member 62, and in this way the individual ribs 88 may be expanded outward to circumscribe the heating element 72 by simply pushing in a distal direction on the proximal end of cylinder 80. The non-expanded configuration of the cage region is illustrated in FIGS. 5 and 7, while the expanded configuration of the cage region 82 is illustrated in FIGS. 6 and 8. Alternatively, the axial members 86 may be fabricated from a resilient material, such as "spring" steel and initially formed in the expanded configuration of FIG. 8. The axial members 86 can then be maintained in the radially collapsed configuration of FIG. 7 simply by maintaining axial tension on the cylinder 80 and expansion can be effected by releasing such tension.

As best observed in FIG. 6, expansion of the ribs 86 defines a cage structure having relatively large apertures or openings 90 between adjacent ribs. In this way, substantially free circulation of a thermally conducting medium may be achieved while the ribs protect the heating element from direct contact with the internal wall of the hollow body organ.

Figure 9:
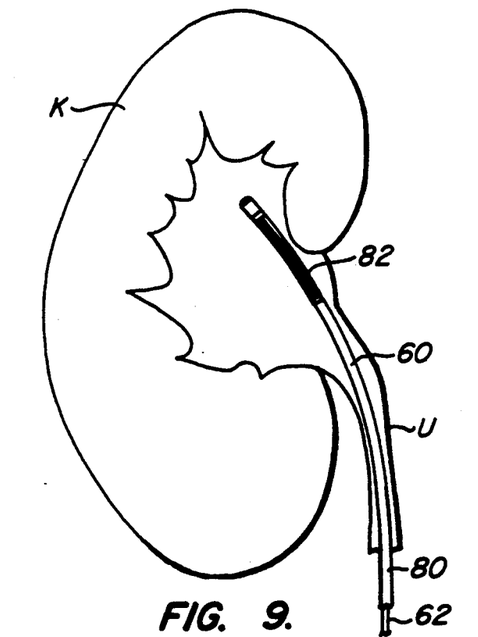
FIGS. 9 and 10 illustrate the method of the present invention using the catheter of FIG. 5 to heat the interior of a kidney.
Figure 10:
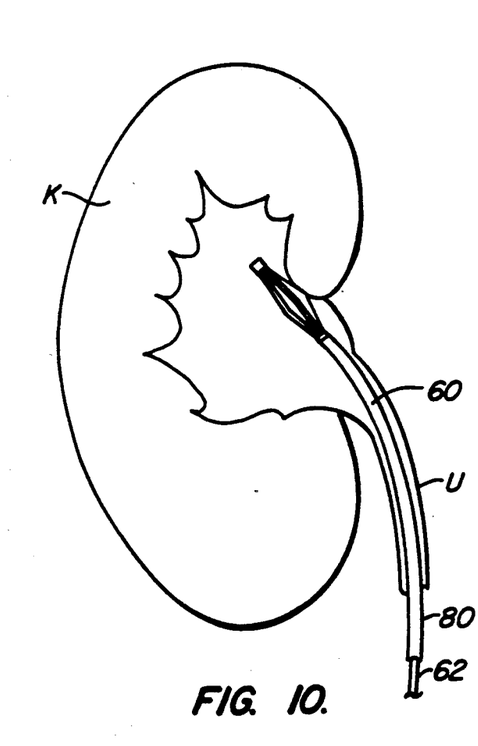

Referring now to FIGS. 9 and 10, use of the catheter 60 for thermally treating a kidney K is illustrated. The catheter 60 may be introduced through the ureter U in a retrograde direction. Catheter 60 will be inserted so that the heater 72 within cage region 82 lies within the interior of the kidney K. As illustrated in FIG. 9, the shield region 82 is in its collapsed configuration and is generally in contact with an interior wall of the kidney K. The heater 72 may be spaced apart from the interior wall of the kidney K simply by urging the cylinder 80 in a proximal direction relative to the first flexible member 62, causing compression of the cage region and radial expansion of the individual ribs. Heat may then be safely applied through the heating element 72 with the assurance that the heating element will not directly contact the internal wall of the kidney.

Figure 11:
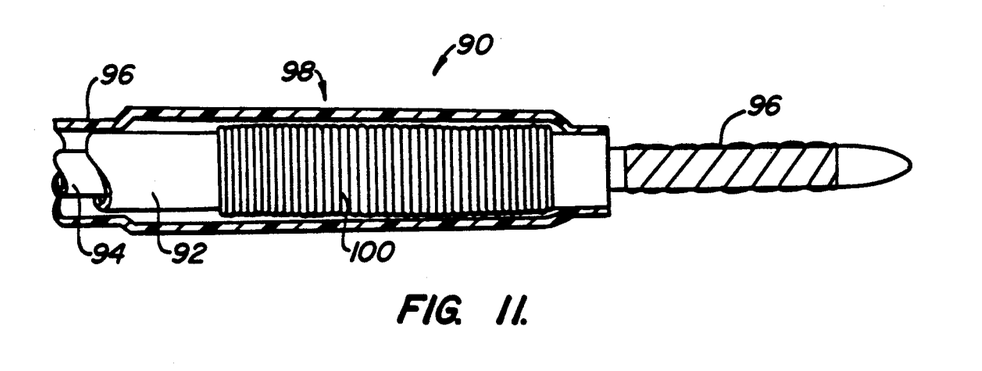
FIG. 11 illustrates a preferred embodiment of the catheter of the present invention incorporating both a movable heating element and an expandable shield about the heating element.

A catheter 90 having a preferred construction which incorporates both the occlusion means and protective cage, as described above, is illustrated in FIG. 11. The catheter 90 includes a first flexible elongate member 92 and a second flexible elongate member 94, the latter including an inflatable balloon 96 (shown in its deflated configuration) at its distal end. A cylinder 96 is disposed about the exterior of first flexible elongate member 92 and includes shield region 98 near its distal end circumscribing a heater element 100 (wrapped about first member 92). The details of construction and use of the catheter will be generally as described above in connection with the two previous embodiments.

Figure 12:
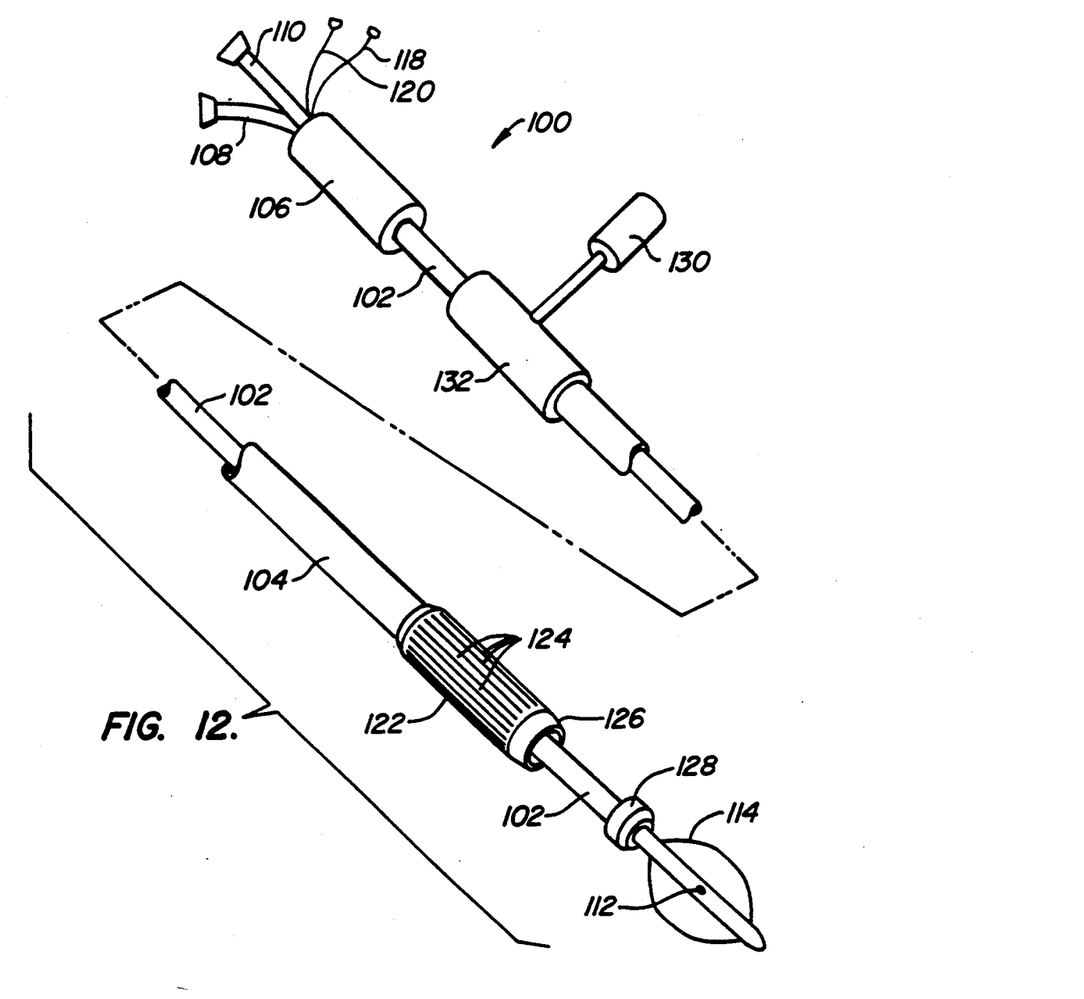
FIG. 12 illustrates a preferred embodiment of the catheter of the present invention incorporating a rotatable shield element which is suitable for mixing of a thermally conductive medium within a hollow body organ.
Figure 13:
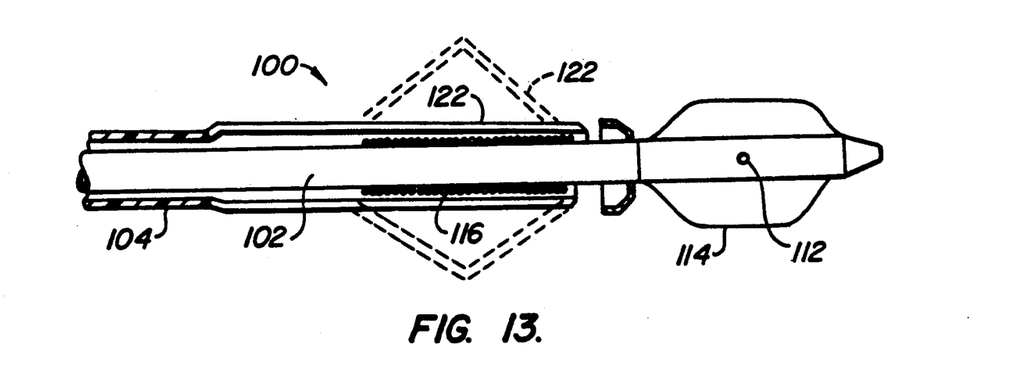
FIG. 13 is a detailed elevational view of the distal end of the catheter of FIG. 12, shown in cross-section.

Referring now to FIGS. 12 and 13 a third embodiment 100 of the catheter of the present invention includes a first flexible elongate member 102, a second flexible elongate member 104, and a proximal housing 106 attached at a distal end of the first member. The proximal housing 106 includes a first connector 108 which provides access to a central lumen in the first member 102 and a second connector 110 which provides access to a balloon inflation lumen (not illustrated) also in the first member. The balloon inflation lumen terminates in a balloon inflation port 112 disposed within inflatable balloon 114 formed over a portion of the distal end of first member 102.

A heater coil 116 (FIG. 13) is wound over the exterior of the distal end of first member 102 generally as described above for the other embodiments of the catheter of the present invention. Connecting wires 118 and 120 are brought out through the proximal housing 106 to allow connection of the coil 116 to an external power source (not illustrated).

An expandable shield or cage 122 is formed at the distal end of the second elongate member 104, typically but not necessarily being integrally formed in the member by providing a plurality of axial cuts or slits 124.

The shield 122 may be radially expanded to the configuration shown in broken line in FIG. 13 by axially translating the second elongate member 104 in a forward (distal) direction so that a forward chamfered surface 126 engages a stop member 128 secured about the first elongate member 102.

The stop member 128 serves as a bearing member for the chamfered surface 126 so that the entire second elongate member 104 can be rotated about its axial center line. Conveniently, a drive motor 130 can be mounted on a gear rotator 132 which can rotate the second elongate member 104 at a desired rate, typically from about 20 rpm to 200 rpm. In this way, the expanded cage 122 can act as an agitator in order to enhance the transfer of heat from the heater coil 116 throughout the interior of the hollow body organ being treated.

As illustrated in FIGS. 12 and 13, the heater 116 is mounted on the first flexible elongate member 102. For that reason, the heater 116 will remain fixed in place so long as balloon 114 is located in a desired position. Such construction is advantageous as it allows electrical connectors 118 and 120 to be disposed on a non-rotating member, greatly facilitating their connection. It would, of course, be possible to attach the heating coil to second member 104 within the cage region 122 if it is desired to provide a rotatable cage and heater which can be repositioned relative to the balloon 112.

The remaining structured features and manner of use of the catheter 100 are generally comparable to those described above for the alternate embodiments.

Although the foregoing invention has been described in detail for purposes of clarity of understanding, it will be obvious that certain modifications may be practiced within the scope of the appended claims.

What is claimed is:

1. A catheter for heating a hollow body organ, said catheter comprising:

a first flexible elongate member having a proximal end, a distal end, and an axial lumen extending between said proximal and distal ends;

a second flexible elongate member slidably disposed within the axial lumen of the first flexible elongate member;

means disposed externally near the distal end of the first flexible elongate member for heating an environment surrounding the catheter; and means on the second flexible elongate member for sealing a region connecting with the hollow body organ.

2. A catheter as in claim 1, wherein the means for sealing includes an inflatable balloon.

3. A catheter as in claim 1, having an annular lumen between the first and second flexible elongate members.

4. A catheter as in claim 1, further comprising a shield and means on the first flexible elongate member for expanding the shield about the heating means while the heating means is positioned within the hollow body organ.

5. A catheter as in claim 1, wherein the means for heating on the first flexible elongate member comprises a coil resistance heater disposed externally on the member.

6. A catheter as in claim 5, wherein the coil resistance heater extends over a length in the range from about 3 mm to 6 cm.

7. A catheter for heating a hollow body organ, said catheter comprising:

a first flexible elongate member having a proximal end, a distal end, and an axial lumen extending between said proximal and distal ends;

a second flexible elongate member slidably disposed within the axial lumen of the first flexible elongate member, said second flexible elongate member being a flexible tubular structure having an axial lumen available for perfusion or aspiration and having sufficient column strength to act as a guide for axially positioning the first flexible elongate member thereover;

means on the second flexible elongate member for sealing a region connecting with the hollow body organ; and means disposed externally near the distal end of the first flexible elongate member for heating an environment surrounding the catheter.

8. A catheter as in claim 7, wherein the means for sealing includes an inflatable balloon.

9. A catheter as in claim 7, having an annular lumen between the first and second flexible elongate members.

10. A catheter as in claim 7, further comprising a shield and means on the first flexible elongate member for expanding the shield about the heating means while the heating means is positioned within the hollow body organ.

11. A catheter as in claim 7, wherein the means for heating on the first flexible elongate member comprises a coil resistance heater disposed externally on the member.

12. A catheter as in claim 11, wherein the coil resistance heater extends over a length in the range from about 3 mm to 6 cm.

13. A method for heating a hollow body organ, said method comprising:

(a) placing a distal end of a second flexible elongate member within the hollow body organ;

(b) positioning a first flexible elongate member over the second flexible elongate member so that a heater on said first flexible elongate member lies within a first desired region within the hollow body organ;

(c) heating the first desired region with the heater;

(d) repositioning the first flexible elongate member over the second flexible elongate member so that the heater lies within a second desired region within the hollow body organ; and (e) heating the second desired region with the heater.

14. A method as in claim 13, further comprising repeating steps (d) and (e) for at least a third desired region within the hollow body organ.

15. A method as in claim 13, wherein the first desired region is a region connecting to the hollow body organ.

16. A method as in claim 15, wherein the hollow body organ is the gallbladder and the connecting region is the cystic duct.

17. A method as in claim 16, wherein a balloon at the distal end of the second flexible elongate member is inflated within the connecting region.

18. A catheter for heating a hollow body organ, said catheter comprising:

a first flexible elongate member having a proximal end, a distal end, and an axial lumen extending between said proximal and distal ends;

a second flexible elongate member slidably disposed within the axial lumen of the first flexible elongate member; and means disposed externally near the distal end of the first flexible elongate member for heating an environment surrounding the catheter, said heating means comprising an exposed convective heating surface which is free from surrounding structure.

19. A catheter as in claim 18, wherein the second flexible elongate member further comprises a means for sealing a region connecting with the hollow body organ.

20. A catheter as in claim 19, wherein the means for sealing includes an inflatable balloon.

21. A catheter as in claim 18, having an annular lumen between the first and second flexible elongate members.

22. A catheter as in claim 18, wherein the means for heating on the first flexible elongate member comprises a coil resistance heater disposed externally on the member.

23. A catheter as in claim 22, wherein the coil resistance heater extends over a length in the range from about 3 mm to 6 cm.

24. A catheter for heating a hollow body organ, said catheter comprising:

a first flexible elongate member having a proximate end, a distal end, and an axial lumen extending between said proximal and distal ends;

a second flexible elongate member slidably received within the axial lumen of the first flexible elongate member;

means disposed on the second flexible elongate member for heating an environment surrounding the catheter;

a stop element disposed near the distal end of the second flexible elongate member;

a shield disposed about the heating means on the second flexible member; and means on the first flexible elongate member for expanding the shield about the heating means on the second flexible elongate member by axially advancing the first member against the stop element on the second member;

whereby the second flexible elongate member may be rotated relative to the first in order to enhance mixing of a thermally conductive fluid within the hollow body organ.

25. A catheter as in claim 24, further comprising an inflatable balloon disposed distally of the stop element on the second flexible elongate member.

26. A catheter as in claim 24, wherein the means for heating on the first flexible elongate member comprises a coil resistance heater disposed externally on the member.

27. A method for heating a hollow body organ, said method comprising:
 (a) placing a distal end of a flexible member within the hollow body organ;
 (b) expanding a shield over the distal end of the flexible member;
 (c) energizing a heating element within the expanded shield; and
 (d) rotating the shield in order to enhance mixing of a thermally conductive fluid within the hollow body organ.

28. A method as in claim 27, further comprising positioning the flexible member over another flexible member which has been previously located within the hollow body organ.

29. A method as in claim 28, still further comprising expanding a balloon on said another flexible member to occlude a region connecting with the hollow body organ.

30. A catheter for heating a hollow body organ, said catheter comprising:
 a first flexible elongate member having a proximal end, a distal end, and means for heating a fluid environment surrounding the catheter to a temperature sufficient to thermally ablate the internal surface of a body organ, said heating means being disposed externally near the distal end of the first flexible member;
 an expandable shield disposed about the heating means which can assume a collapsed configuration and an expanded configuration and which possesses a plurality of large apertures, which, in the expanded configuration, the apertures are sufficiently large to permit free circulation of a fluid to and from the environment, whereby heated fluid in the environment surrounding the heating means can circulate and transfer heat to the body organ; and
 means on the first flexible elongate member for expanding the shield about the heating means while the heating means is positioned within the hollow body organ.

31. A catheter as in claim 30, wherein the shield comprises a cylinder having a plurality of axial slits and the means for expanding the shield comprises means for compressing said cylinder to cause outward deformation thereof.

32. A catheter as in claim 31, wherein the means for compressing the cylinder comprises a flexible tubular member which extends over the length of the flexible elongate member.

33. A catheter as in claim 32, further comprising means on the first flexible elongate member for limiting movement of the flexible tubular member so that the cylinder can be compressed by pushing the tubular member in the distal direction relative to the elongate member.

34. A catheter as in claim 30, wherein the means for heating on the first flexible elongate member comprises a coil resistance heater disposed externally on the member.

35. A catheter as in claim 34, wherein the coil resistance heater extends over a length in the range from abut 3 mm to 6 cm.

36. A catheter as in claim 30, wherein the first flexible elongate member has an axial lumen extending from its proximal end to its distal end, said catheter further comprising:
 a second flexible elongate member slidably disposed within the axial lumen of the first flexible elongate member; and
 an inflatable balloon disposed near the distal end of the second flexible elongate member, whereby the heating means may be positioned by axially translating the first flexible elongate member over the second flexible elongate member.

37. A method for heating a hollow body organ, said method comprising:
 introducing a distal end of a flexible elongate member to the interior of the hollow body organ;
 expanding a shield about an external heating element near the distal end of the flexible elongate member after said member has been introduced, said shield having apertures to allow free circulation of fluid therethrough in both directions;
 introducing a thermally conductive medium into and circulating said medium within the interior of the hollow body organ; and
 raising the temperature of the heating element to heat the thermally conductive medium sufficiently to ablate an interior surface of the body organ, while the shield prevents contact between the external heating element and the interior surface of the organ.

38. A method as in claim 37, wherein the shield is a cylinder having a plurality of axial slits and the shield is expanded by compressing the length of the cylinder.

39. A method as in claim 38, wherein the cylinder is formed at the distal end of a flexible tubular ember which extends over the length of the flexible elongate member, whereby the cylinder may be compressed by pushing on a proximal end of the tubular member.

40. A method as in claim 37, wherein the shield is a cylinder having a plurality of axial slits and the shield is expanded by releasing tension which allows the shield to assume an unconstrained expanded configuration.

41. A catheter for heating a hollow body organ, said catheter comprising:
 a first flexible elongate member having a proximal end, a distal end, and an axial lumen extending between said proximal and distal ends;
 a second flexible elongate member slidably disposed within the axial lumen of the first flexible elongate member; said first and second elongate members together defining an annular lumen which is open at its distal end to permit perfusion or aspiration of fluids therethrough;
 means disposed externally near the distal end of the first flexible elongate member for heating an environment surrounding the catheter; and
 a shield, comprising a plurality of expandable ribs disposed about the heating means and means on the first flexible elongate member for expanding the shield while the heating means is positioned within the hollow body organ.

42. A catheter as in claim 41, wherein the second flexible elongate member further comprises a means for sealing a region connecting with the hollow body organ.

43. A catheter as in claim 42, wherein the means for sealing includes an inflatable balloon.

44. A catheter as in claim 41, wherein the means for heating on the first flexible elongate member comprises a coil resistance heater disposed externally on the member.

45. A catheter as in claim 44, wherein the coil resistance heater extends over a length in the range from about 3 mm to 6 cm.

* * * * *